US00PP11813P2

(12) United States Plant Patent
van Rijn

(10) Patent No.: US PP11,813 P2
(45) Date of Patent: Mar. 13, 2001

(54) ANTHURIUM PLANT NAMED 'RED QUEEN'

(75) Inventor: Leonardus van Rijn, Schipluiden (NL)

(73) Assignee: RijnPlant, Schipluiden (NL)

( * ) Notice: Under 35 U.S.C. 154(b), the term of this patent shall be extended for 0 days.

(21) Appl. No.: 09/291,096

(22) Filed: Apr. 14, 1999

(51) Int. Cl.[7] ..... A01H 5/00

(52) U.S. Cl. ..... Plt./365

(58) Field of Search ..... Plt./365, 369

(56) References Cited

PUBLICATIONS

UPOV–ROM GTITM Computer Database 1999/02, GTI Jouve Retrieval Software, citation for 'Red Queen', May 29, 1998.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Anthurium plant named 'Red Queen', characterized by its upright and outwardly spreading plant habit; freely clumping growth habit; large dark green leaves that are ovate to lanceolate in shape; numerous spathes that are positioned upright and beyond the foliage on strong and erect scapes; large, durable, glossy red spathes; year-round continuous flowering; good flowering performance under low light conditions; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name 'Red Queen'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor in October, 1994 of the Inventor's proprietary *Anthurium andreanum* selection code number 92-4 as the female, or seed, parent with the Inventor's proprietary *Anthurium andreanum* selection code number 94-3 as the male, or pollen, parent. The cultivar 'Red Queen' was discovered and selected by the Inventor as a plant within the progeny of the stated cross in a controlled environment in Schipluiden, The Netherlands in January, 1997.

Asexual propagation of the new culitvar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Red Queen'. These characteristics in combination distinguish 'Red Queen' as a new and distinct cultivar:

1. Upright and outwardly spreading plant habit.

2. Freely clumping growth habit.

3. Large dark green leaves that are ovate to lanceolate in shape.

4. Numerous spathes that are positioned upright and beyond the foliage on strong and erect scapes.

5. Large, durable, glossy red spathes.

6. Year-round continuous flowering.

7. Good flowering performance under low light conditions.

8. Good post-production longevity.

The new Anthurium can be compared to the female parent, the Inventor's proprietary selection code number 92-4. In side-by-side comparisons conducted by the Inventor in Schipluiden, The Netherlands, plants of the new Anthurium differ from plants of selection code number 92-4 in the following characteristics:

1. Plants of the new Anthurium are more compact than plants of the selection code number 92-4.

2. Plants of the new Anthurium have larger leaves than plants of the selection code number 92-4.

3. Plants of the new Anthurium have larger spathes than plants of the selection code number 92-4.

The new Anthurium can be compared to the male parent, the Inventor's proprietary selection code number 94-3. In side-by-side comparisons conducted by the Inventor in Schipluiden, The Netherlands, plants of the new Anthurium differ from plants of selection code number 94-3 in the following characteristics:

1. Plants of the new Anthurium are less compact than plants of the selection code number 94-3.

2. Plants of the new Anthurium grow faster than plants of the selection code number 94-3.

3. Plants of the new Anthurium do not have as durable leaves as plants of the selection code number 94-3.

4. Plants of the new Anthurium have red-colored spathes whereas plants of the selection code number 94-3 have pink-colored spathes.

The new Anthurium can be compared to the Anthurium cultivar 'Eveline', disclosed in U.S. Plant Pat. No. 10,970. In side-by-side comparisons conducted by the Inventor in Schipluiden, The Netherlands, plants of the new Anthurium differ from plants of the cultivar 'Eveline' in the following characteristics:

1. Plants of the new Anthurium are more compact than plants of the cultivar 'Eveline'.

2. Plants of the new Anthurium have darker green leaves than plants of the cultivar 'Eveline'.

3. Plants of the new Anthurium have smaller spathes than plants of the cultivar 'Eveline'.

4. Plants of the new Anthurium and of the cultivar 'Eveline' differ in spathe coloration.

BRIEF DESCRIPTION OF THE PHOTOGRAPH

The accompanying colored photograph illustrates the overall appearance of the new Anthurium, showing the colors as true as it is reasonably possible to obtain in colored reproductions of this type.

The photograph comprises a top perspective view of a typical potted plant of the cultivar 'Red Queen'. Leaf, spathe and spadix colors in the photograph may appear different from the actual colors due to light reflectance.

DETAILED BOTANICAL DESCRIPTION

In the following description, color references are made to The Royal Hoticultural Society Colour Chart except where general terms of ordinary dictionary significance are used. The following observations and measurements described 2.5-years old plants grown in 30-cm containers in Schipluiden, The Netherlands, in a glass greenhouse with an average day temperature of 25° C. and an average night temperature of 19° C.

Botanical classification: *Anthurium andreanum* cultivar, 'Red Queen'.

Parentage:

*Female parent.*—Inventor's proprietary *Anthurium andreanum* selection code number 92-4.

*Male parent.*—Inventor's proprietary *Anthurium andreanum* selection code number 94-3.

Propagation:

*Method.*—By tissue culture.

*Time to develop roots.*—About 70 or 84 days at 24° C. or 21° C., respectively are required to root a tissue-cultured plantlet.

*Rooting habit.*—Numerous and very strong fleshy roots.

Plant description:

*Plant shape.*—Upright, inverted triangle, symmetrical.

*Growth habit.*—Freely clumping, bushy and dense. Appropriate for 17 to 40-cm containers.

*Plant height.*—About 60 cm from soil level to leaf plane and about 60 to 80 cm from soil level to apex of spathes.

*Plant width.*—About 100 to 120 cm.

*Plant vigor.*—High.

*Growth rate.*—Rapid.

*Crop time.*—About 8 and 16 months are usually required from planting of young plants to finished plants in 17 and 40-cm containers, respectively.

*Foliage description.*—Quantity: Usually about three to five per shoot. Length: About 30 to 35 cm. Width: About 17 to 20 cm. Shape: Ovate to lanceolate. Apex: Apiculate to cuspidate. Base: Strongly auriculate; lobes not overlapping. Margin: Entire; slightly undulating. Texture: Smooth, glabrous, leathery. Color: Young leaves, upper surface: 146A to 147A; glossy. Young leaves, lower surface: 146C to 144A with gray flush. Mature leaves, upper surface: Darker than 137A; less glossy than young leaves. Mature leaves, lower surface: 146C to 144A. Petiole: Length: About 25 to 55 cm. Color: Close to 146B, slight anthocyanin, purplish. Geniculum length: About 2 to 4 cm. Geniculum diameter: About 6 to 8 mm. Geniculum color: 144A.

Inflorescence description:

*Inflorescence arrangement.*—Spathes with spadices held beyond the foliage. Flowering structures arise form leaf axis. Freely flowering; continuous flowering year-round; numerous spathes/spadices per plant.

*Inflorescence longevity.*—Spathes/spadices last about six weeks under winter conditions and about three months under summer conditions; persistent.

*Flowers.*—Quantity per spadix: Numerous, about 150 to 200. Shape: Rounded. Diameter: About 1 mm, maximum.

*Spathe.*—Length: About 12 to 15 cm. Width: About 11 to 13 cm. Shape: Cordate. Apex: Apiculate to cuspidate. Base: Strongly auriculate, lobes not overlapping. Margin: Entire. Texture: Leathery, glabrous, moderate to significant blistering, glossy. Color: When opening: 44B to 45B. Front surface: 44B to 45B. Back surface: 47C. After senescence: 47B.

*Spadix.*—Length: About 7 to 9 cm. Diameter: Midsection, about 10 mm; apex, about 8 mm. Shape: Columnar. Cross section: Rounded. Longitudinal axis: Very weakly recurved. Color: Base and midsection: 158A. Apex: 24A. After senescence: 146A to 146B.

*Scape.*—Length: About 50 to 60 cm. Aspect: Strong and erect. Color: 144A, anthocyanin towards apex, purplish.

*Reproductive organs.*—Androecium: Pollen color: Creamy white, 158D. Gynoecium: Stigma shape: Ovoid. Ovary: Protogyneous.

Disease resistance: Plants of the new Anthurium have exhibited good resistance to diseases common to Anthurium.

Seed development: Seed development on plants of the new Anthurium has not been observed.

It is claimed:

1. A new and distinct cultivar of Anthurium plant named 'Red Queen', as illustrated and described.

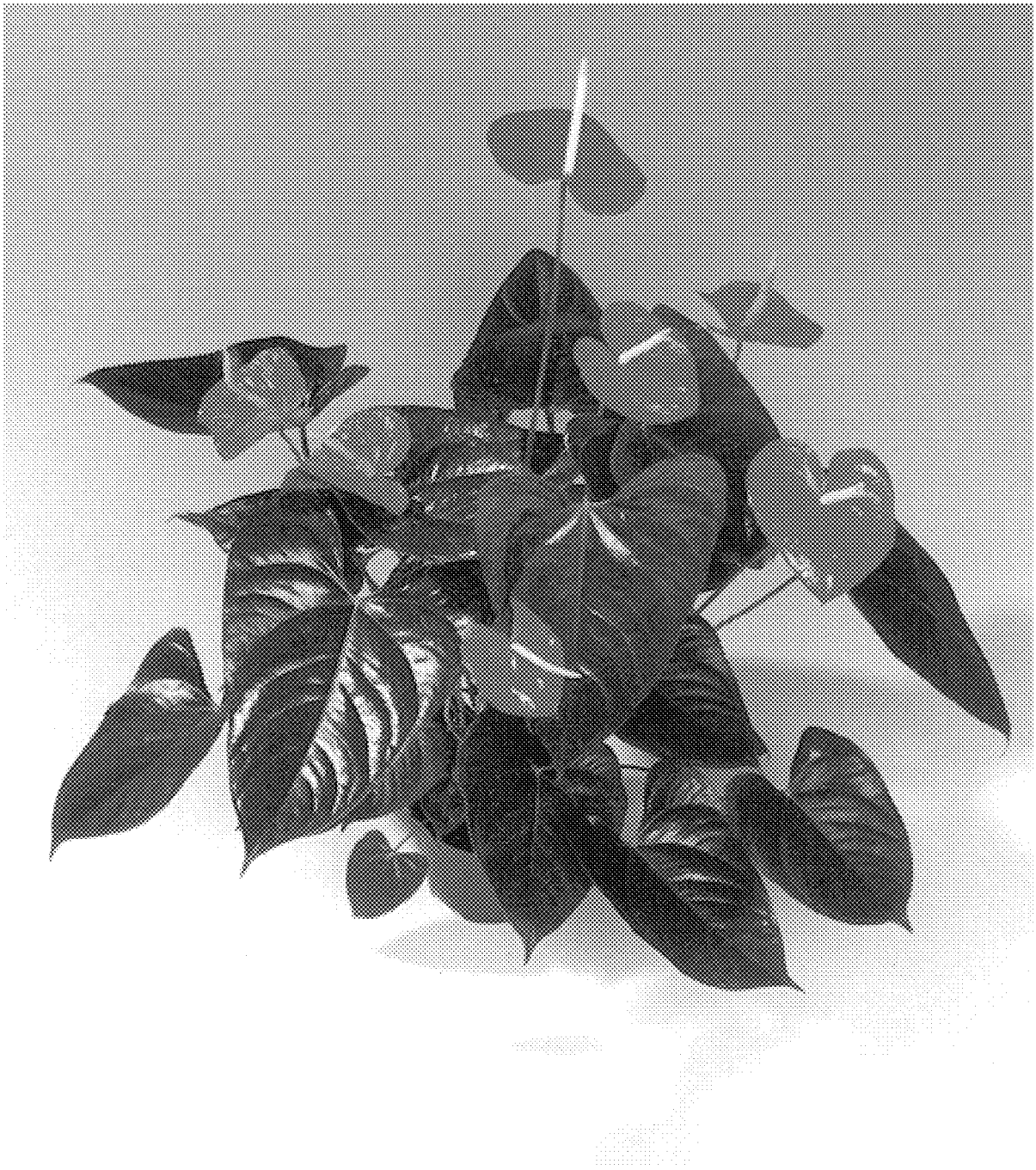

* * * * *